United States Patent
Keeping et al.

(10) Patent No.: US 6,689,602 B2
(45) Date of Patent: Feb. 10, 2004

(54) BIO-SENSOR

(75) Inventors: Sean Crispian Keeping, Shortlands (GB); Dieter Binz, Ladenburg (GB); Colin Ernest Howell, St. Neots (GB); Leslie Jamson, Cheltenham (GB); Robert Arthur Mead, St. Neots (GB); Charles Lucas Greensted, Cheltenham (GB); David Edward Coe, St. Neots (GB)

(73) Assignee: ABB Automation Limited, Stevenage (GB)

( * ) Notice: Subject to any disclaimer, the term of this patent is extended or adjusted under 35 U.S.C. 154(b) by 258 days.

(21) Appl. No.: 09/867,742

(22) Filed: May 31, 2001

(65) Prior Publication Data

US 2002/0015992 A1 Feb. 7, 2002

(30) Foreign Application Priority Data

May 31, 2000 (GB) .............................................. 0013214

(51) Int. Cl.[7] .............................................. C12M 1/34

(52) U.S. Cl. ................................ 435/287.1; 435/287.4; 435/287.5

(58) Field of Search .......................... 422/79; 435/287.1, 435/287.4, 287.5

(56) References Cited

U.S. PATENT DOCUMENTS 5,589,133 A * 12/1996 Suzuki ........................ 422/79
6,461,861 B2 * 10/2002 Schillig et al. .......... 435/287.1

FOREIGN PATENT DOCUMENTS

| EP | 0360276 | 3/1990 |
| EP | 0543407 A1 | 5/1993 |
| WO | WO 98/53045 | 5/1998 |

* cited by examiner

Primary Examiner—David A. Redding
(74) Attorney, Agent, or Firm—Larson & Taylor, PLC

(57) ABSTRACT

A compact bio-sensor is provided, particularly suitable for measuring biological oxygen demand, which includes micro-organisms for altering a biological parameter and sensors upstream and downstream of the organisms.

20 Claims, 2 Drawing Sheets

BIO-SENSOR

The present invention relates to bio-sensors, particularly, but not exclusively, to sensors for measuring parameters such as biological oxygen demand.

Our earlier International Application WO-A-98/53045 discloses a microbial membrane reactor for use in flow systems which provides an effective means for carrying out a process in which microorganisms interact with a flowing fluid. The entire disclosure of that document is incorporated herein by reference.

It is an aim of the present invention to provide a compact device for sensing a biological parameter.

According to a first aspect, the invention provides a sensor comprising:

means for receiving a fluid;
means for directing the fluid into contact with microorganisms selected to interact with suspected components of the fluid to alter at least one property of the fluid and therefrom to means for sensing said at least one property.

In a preferred application, the sensor is a biological oxygen demand sensor, said at least one property is oxygen content and the microorganisms are selected to react with nutrients in the fluid and thereby consume oxygen.

In one embodiment, the sensor includes means for sensing said at least one property prior to interaction with the microorganisms. In this way, a measure of the change in the property can be obtained from the difference of the outputs of the "before" and "after" sensors.

More preferably, the sensor is arranged so that said at least one property has substantially a known value prior to interaction with the microorganisms.

Preferably, in the case of a biological oxygen demand sensor, the sensor includes means for establishing substantially a predetermined concentration of oxygen in the fluid prior to interaction with the microorganisms. For example, the sensor may include means for establishing substantial equilibrium between dissolved oxygen levels in the fluid and an atmosphere of substantially known oxygen concentration, typically ambient air. The means for establishing equilibrium may comprise a gas-permeable membrane exposed on one side to the fluid and on the other to the atmosphere, the membrane being formed preferably of PTFE.

The microorganisms are preferably trapped between opposed membranes or a membrane and a support, preferably in a manner similar to that described in our earlier International Application No. WO-A-98/53045, the entire disclosure of which has already been incorporated by reference and to which reference should be made for details of a suitable device for contacting fluid with microorganisms.

The sensor is preferably integrated within a housing. Preferably, the sensor comprises a main body component; a first cover member disposed over at least a portion of a surface of the main body component, the first cover member and body component together defining a biological reaction chamber for containing said microorganisms; and a second cover member disposed over a further portion of a surface of the main body component, the second cover member and main body member together defining a cavity containing said means for sensing said at least one parameter; wherein the sensor further has means defining fluid conduits for conducting fluid from a fluid inlet to the biological reaction chamber and from the biological reaction chamber to the sensing means.

Preferably, the main body component has one or more channels formed (for example etched) into the surface thereof in the region of the biological reaction chamber and a porous membrane is provided between the first cover member and the main body component overlying said channel(s) to contain microorganisms in a cavity defined in the first cover member but to allow fluid in the channels to interact with the microorganisms.

In the case of an oxygen or similar sensor, preferably the main body component has one or more channels formed, for example etched, in the surface in the region of the sensing means cavity and a metallised membrane is provided over said channels to separate fluid in the channels from an electrolyte provided in the sensing cavity and to serve as one electrode of the sensing means. The metallised membrane may comprise gold coated PTFE, the electrolyte may comprise potassium chloride and a further electrode of silver may be provided to form an oxygen sensor.

The second cover member may be disposed on the same side of the main body component as the first cover member. More preferably, the first and second cover members are disposed on opposite sides of the main body component, sandwiching the main body component between them. This may make more effective use of the surface area of the main body component. Preferably the components are substantially flat, resulting in a compact sensor. The first cover member may form part of another component, for example a substrate, and the main body component and the second cover member may be formed as layers on the substrate.

Preferably, the sensor is incorporated in a replaceable cartridge of an analysis unit, preferably as described in our concurrently filed co-pending application number which bears attorney reference IK/20665.

An embodiment of the invention will now be described, by way of example only, with reference to the accompanying drawings in which.

Figures 1, 2:
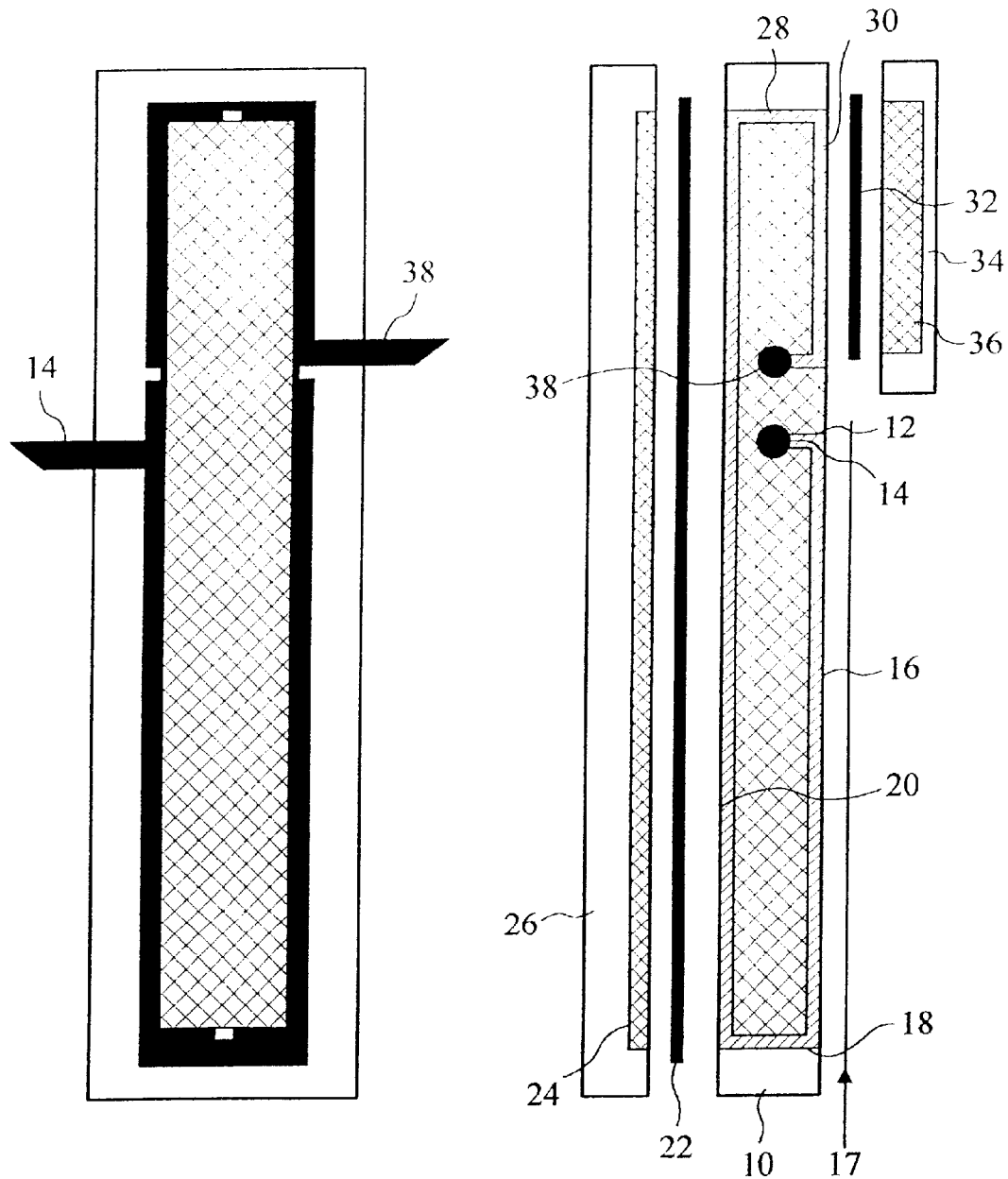
FIG. 1 is a cross-sectional view of a biological oxygen demand sensor.
FIG. 2 is a view from above of the sensor of FIG. 1.

Referring to FIG. 1 a main body component 10 has a channel 12 defined therein leading from inlet 14 over an exposed area of the (upper) surface 16 to a through hole 18 serving to direct fluid to a further exposed area 20 on the opposite (lower) side. The exposed area 16 is covered with a PTFE membrane 17 which allows oxygen from the surrounding atmosphere to diffuse into the fluid. The fluid flowing under the membrane forms a thin layer having a large exposed surface area ensuring that the fluid is thoroughly aerated.

The lower exposed area 20 is covered by a further porous membrane 22, typically of PTFE, which separates the fluid in the exposed area 20 from a cavity 24 containing microorganisms defined in a lower cover member 26. The diagram in FIG. 1 is shown in exploded form and, when assembled, the membrane 22 is sandwiched between the main body component 10 and the lower cover member 26. Again, the fluid flow channel defined under the membrane is thin with a large surface area to promote effective diffusion of fluid into the microorganism cavity.

A further through hole 28 directs fluid which has passed over the microorganism cavity back to the upper side of the main body component 10 and to a further (thin and large surface area) exposed area 30 overlaid by a further membrane 32, typically comprising gold-coated PTFE forming an electrode of an oxygen sensor. As an alternative, the sensor may comprise lead and gold electrodes. Above the membrane a second cover member 34 is positioned defining a cavity 36 containing an electrolyte, typically potassium chloride and containing a further electrode, typically of silver (not shown in FIG. 1). After passing over the oxygen sensor membrane, the fluid is directed to an outlet 38.

As can be seen from FIG. 2, the inlets and outlets are typically in the form of pointed tubes adapted to be inserted into further conduits to form part of an analysis unit.

Figure 3:
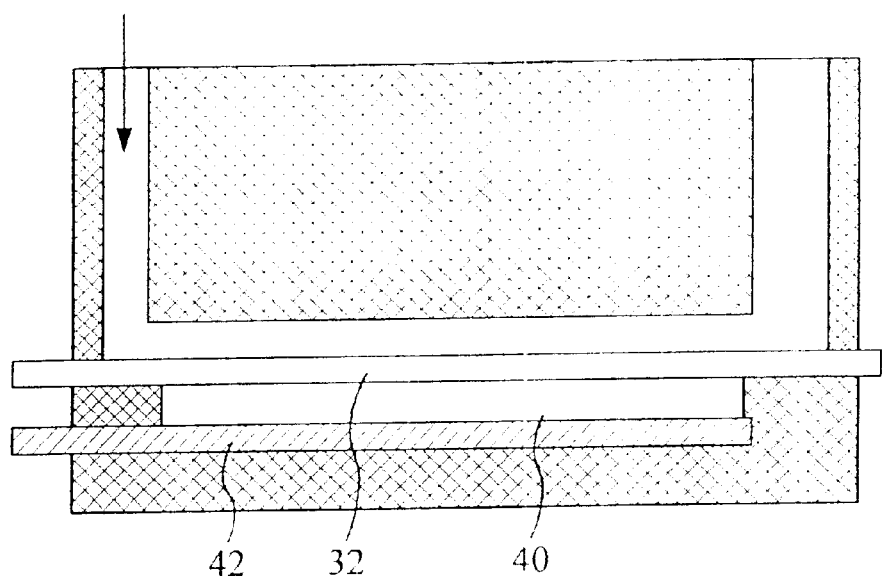
FIG. 3 is an enlarged view of the oxygen sensor of FIG. 1.

Referring to FIG. 3, the operation of the oxygen sensor can be understood better. The fluid whose oxygen content is to be measured passes over the gold-coated membrane 32 behind which is disposed electrolyte 40 and a silver electrode 42 forming an electrochemical cell which produces a potential dependent on the concentration of oxygen in the fluid. The potential developed across the two electrodes can be measured by means of a high-impedance potential-measuring circuit.

Alternative configurations are possible. For example the microorganisms may be in a removable cartridge, separately replaceable from the sensors. The features, particularly the preferred features described above may be provided independently or in any combination. The appended abstract is incorporated herein by reference.

What is claimed is:

1. A sensor comprising:
   means for receiving a fluid;
   means for directing the fluid into contact with microorganisms selected to interact with suspected components of the fluid to alter at least one property of the fluid and therefrom to means for sensing said at least one property; and
   means for sensing said at least one property prior to interaction with the microorganisms.

2. A sensor according to claim 1 arranged as a biological oxygen demand sensor, said at least one property being oxygen content and the microorganisms being selected to react with nutrients in the fluid and thereby consume oxygen.

3. A sensor according to claim 1 arranged so that said at least one property has substantially a known value prior to interaction with the microorganisms.

4. A sensor according to claim 2 arranged so that said at least one property has substantially a known value prior to interaction with the microorganisms.

5. A sensor according to claim 4 including means for establishing substantially a predetermined concentration of oxygen in the fluid prior to interaction with the microorganisms.

6. A sensor according to claim 5 wherein the establishing means comprises means for establishing substantial equilibrium between dissolved oxygen levels in the fluid and an atmosphere of substantially known oxygen concentration.

7. A sensor according to claim 6 wherein the means for establishing equilibrium comprises a gas-permeable membrane exposed on one side to the fluid and on the other to said atmosphere.

8. A sensor according to claim 1 wherein the microorganisms are retained by a fluid permeable membrane.

9. A sensor according to any claim 1 integrated within a housing.

10. W A sensor according to claim 1 comprising a main body component and a bioreactor cover member disposed over at least a bioreactor portion of a surface of the main body component, the bioreactor cover member and body component together defining a biological reaction chamber containing said microorganisms.

11. A sensor according to claim 10 wherein the main body component has at least one fluid flow path defined on the surface thereof in the region of the biological reaction chamber and wherein a porous membrane is provided between the bioreactor cover member and the main body component overlying the or each flow path to contain microorganisms in a cavity defined in the bioreactor cover member but to allow fluid in the channels to interact with the microorganisms.

12. A sensor according to claim 1 comprising a main body component and a sensor cover member disposed over a sensor portion of a surface of the main body component, the sensor cover member and main body member together defining a cavity containing said means for sensing said at least one parameter.

13. A sensor according to claim 12 wherein the main body component has at least one fluid flow path defined on the surface thereof in the region of the sensing means cavity and wherein a metallised membrane is provided overlying the or each flow path to separate fluid in the channels from an electrolyte provided in the sensing cavity and to serve as one electrode of the sensing means.

14. A sensor according to claim 13, wherein the metallised membrane comprises gold coated PTFE.

15. A sensor according to claim 13, wherein the electrolyte comprises potassium chloride.

16. A sensor according to claim 13, wherein a further electrode of silver is provided.

17. A sensor according to claim 13 wherein a further electrode of lead is provided.

18. A sensor according to claim 10 wherein the bioreactor cover member and sensor cover member are disposed on opposite sides of the main body component, sandwiching the main body component between them.

19. A sensor according to claim 10 where including means defining fluid conduits for conducting fluid from a fluid inlet to the biological reaction chamber and from the biological reaction chamber to the sensing means.

20. A sensor according to claim 1 wherein the microorganisms are provided in a replaceable cartridge.

* * * * *